United States Patent [19]

Robbins, III

[11] Patent Number: 4,807,247

[45] Date of Patent: Feb. 21, 1989

[54] TEMPERATURE-CONTROLLED ACCELERATED WEATHERING DEVICE

[75] Inventor: Joseph S. Robbins, III, Phoenix, Ariz.

[73] Assignee: DSET Laboratories, Inc., Phoenix, Ariz.

[21] Appl. No.: 80,551

[22] Filed: Jul. 31, 1987

[51] Int. Cl.$^4$ ............................................. G01N 25/00
[52] U.S. Cl. .................................. 374/57; 73/150 R; 73/865.6; 236/DIG. 9; 356/51
[58] Field of Search .............. 374/33, 9, 57; 126/419; 356/256; 236/DIG. 9; 62/184; 73/150 R, 865.6

[56] References Cited

U.S. PATENT DOCUMENTS

| | | | |
|---|---|---|---|
| 2,945,417 | 7/1960 | Caryl et al. | 126/424 |
| 3,224,266 | 12/1965 | Klippert | 73/150 R |
| 3,327,536 | 6/1967 | Fitzgerald . | |
| 3,500,682 | 3/1970 | Newfield | 73/150 R |
| 3,501,942 | 3/1970 | Fitzgerald et al. . | |
| 3,521,966 | 7/1970 | Archer | 356/256 |
| 3,521,967 | 7/1970 | Archer | 356/256 |
| 3,576,125 | 3/1971 | Kockott et al. . | |
| 3,664,188 | 5/1972 | Kockott | 73/150 R |
| 3,889,531 | 6/1975 | Suga | 73/150 R |
| 4,012,954 | 3/1977 | Klippert | 73/150 R |
| 4,117,712 | 10/1978 | Hager, Jr. | 374/9 |
| 4,222,367 | 9/1980 | Jubb | 126/419 |
| 4,503,902 | 3/1985 | Zolik | 236/DIG. 9 |
| 4,544,995 | 10/1985 | Suga | 73/865.6 X |
| 4,615,481 | 10/1986 | Tanaami et al. | 165/40 X |
| 4,644,166 | 2/1987 | Sturm et al. | 250/372 |
| 4,659,290 | 4/1987 | Kundert | 236/DIG. 9 |
| 4,722,669 | 2/1988 | Kundert | 236/DIG. 9 |
| 4,760,748 | 8/1988 | Katayanagi et al. | 73/865.6 X |

*Primary Examiner*—Daniel M. Yasich
*Attorney, Agent, or Firm*—Cahill, Sutton & Thomas

[57] ABSTRACT

A temperature-controlled accelerated weathering test apparatus concentrates solar radiation upon target samples and controls the flow rate of cooling ambient air circulated across the target samples in order to maintain the target sample temperature substantially constant despite variations in ambient daytime temperature and variations in solar radiation intensity. A temperature sensor is secured to an aluminum panel mounted upon the target board of the test apparatus proximate to the target samples for generating an electrical signal relating to the temperature of the target samples. The temperature sensor and related aluminum panel are coated black to enhance absorbtion of solar radiation. A controller responsive to the electrical signal generated by the temperature sensor controls the application of electrical power to a blower motor used to circulate cooling ambient air across the target samples. The controller increases the speed of the blower motor when the sensed temperature of the target samples is above a predetermined set point, and decreases the speed of the blower motor when the sensed temperature of the target samples is below the predetermined set point.

10 Claims, 3 Drawing Sheets

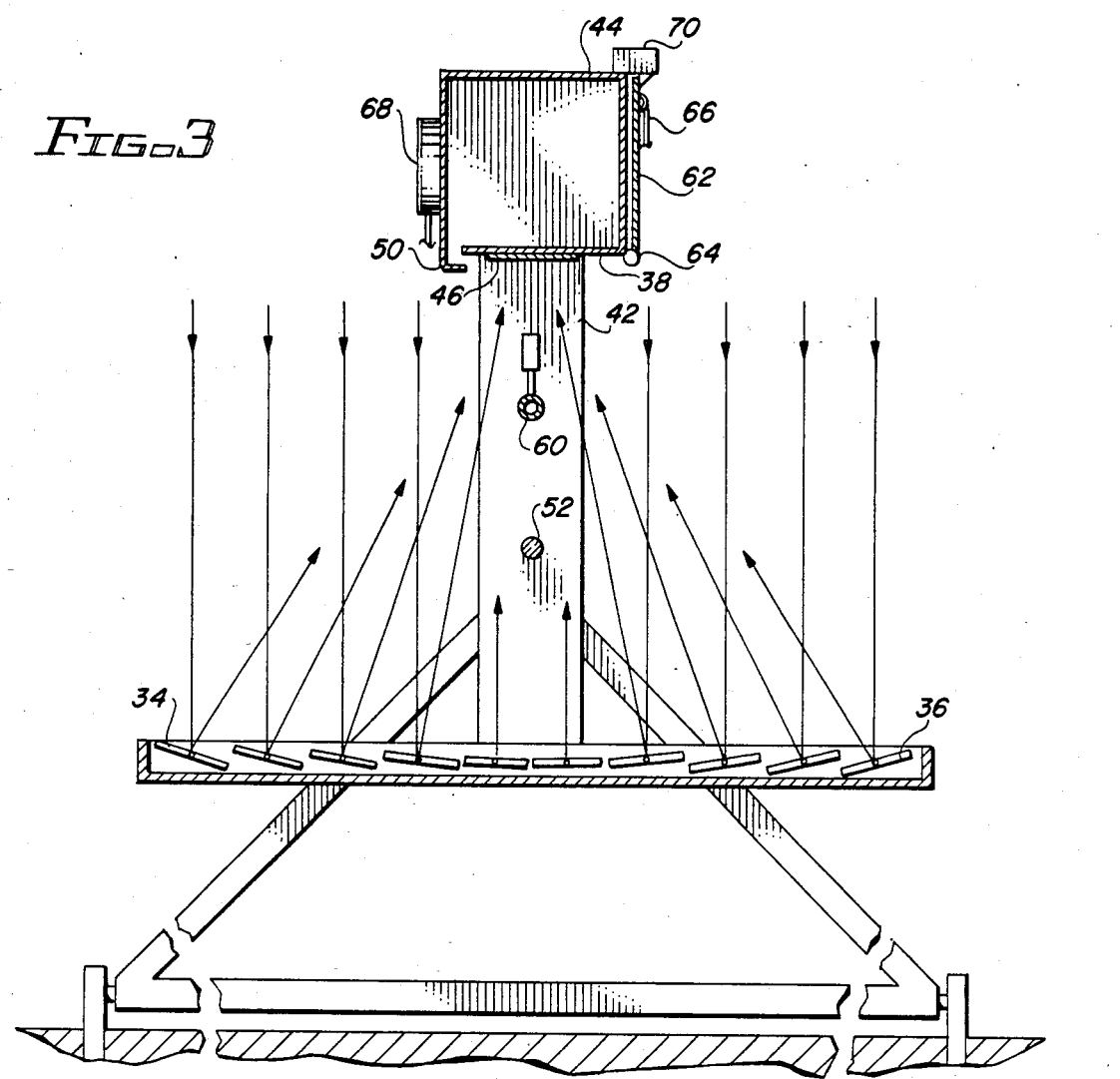
FIG. 3
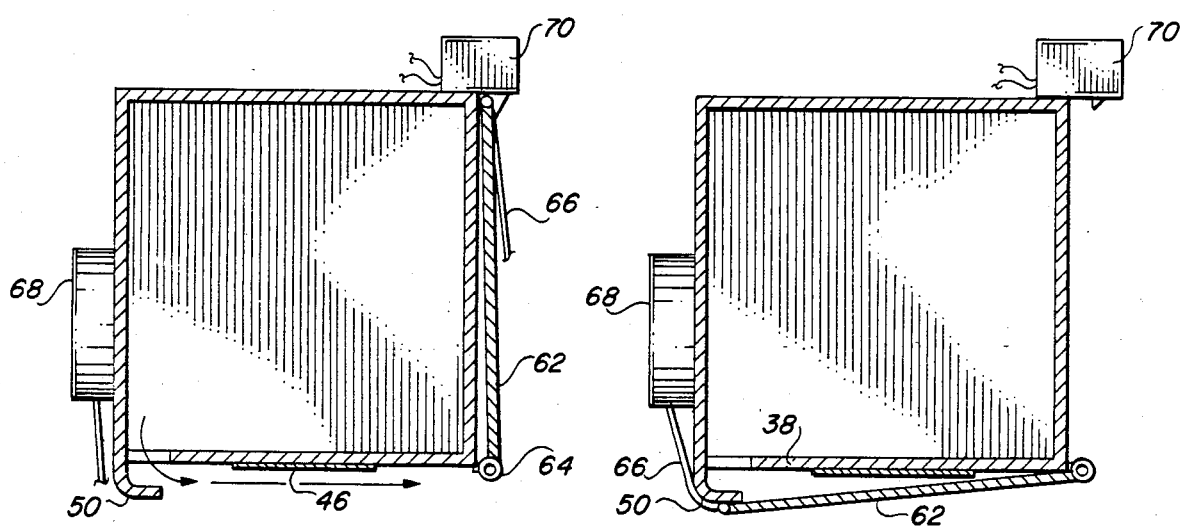
FIG. 4
FIG. 5

TEMPERATURE-CONTROLLED ACCELERATED WEATHERING DEVICE

BACKGROUND OF THE INVENTION

1. Field of the Invention

The present invention relates generally to accelerated weathering test devices of the type used to expose test samples of exterior coatings such as paints and finishes, as well as fabrics and other materials to solar radiation and other weathering effects on an accelerated basis, and more particularly, to such an accelerated weathering test device adapted to maintain a substantially uniform test sample temperature during daylight hours, despite variations in ambient air temperature and variations in solar radiation intensity.

2. Description of the Prior Art

Manufacturers of exterior coatings such as paints and finishes, as well as plastics, and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

One known accelerated weathering test device is disclosed in U.S. Pat. No. 2,945,417 issued to Caryl, et al. The aforementioned test device includes a Fresnel-reflecting solar concentrator having a series of ten flat mirrors which focus natural sunlight onto a series of test samples secured to a target board measuring approximately five inches wide by fifty-five inches long. The Fresnel-reflecting solar concentrator directs solar radiation onto the target board area with an intensity of approximately eight suns. Both the bed which supports the mirrors of the solar concentrator, and the target board, are supported by a frame which can be rotated to follow daily movements of the sun. A solar tracking mechanism responsive to the position of the sun, controls the operation of an electric motor that is used to rotate the test apparatus to follow movements of the sun. The axis of rotation of the test machine is oriented in a north-south direction, with the north elevation having altitude adjustment capability to account for variation in the sun's altitude at various times during the year. Such known testing devices are also provided with an air tunnel mounted above the target board. An air deflector causes air escaping from the air tunnel to be circulated across the test samples mounted to the target board to prevent the test samples from overheating due to the concentrated solar radiation to which they are exposed. A squirrel cage blower communicates with the air tunnel for blowing cooling ambient air therethrough. In addition, water spray nozzles are provided proximate to the target board for wetting the test samples at periodic intervals to simulate the weathering effects of humidity, dew, rain, etc.

Standardized testing methods have been developed for operating accelerated weathering test devices of the type described above. The American Society for Testing and Materials (ASTM) has issued Standards G90, E838, D4141, and D4364 covering the testing procedures and the operating parameters for conducting such outdoor accelerated weathering tests.

Apart from outdoor accelerated weathering test devices of the type described above, other test devices are also known which utilize an artificial source of radiation to expose the test samples. An example of such a test device is disclosed in U.S. Pat. No. 3,664,188, issued to Kockott. While such test devices have the advantage of permitting precise control over radiation intensity, temperature, and humidity, such test devices often fail to duplicate the actual light spectrum of natural sunlight to which the samples under test will actually be exposed in everyday use.

Outdoor accelerated weathering test devices of the type described above in regard to U.S. Pat. No. 2,945,417, have the advantage of using natural sunlight, and hence the samples under test are exposed to the actual spectrum of sunlight. However, one disadvantage of outdoor accelerated weathering test devices has been discovered, namely, that the temperature of the samples under test can vary widely during daylight hours over the course of a day and from one season to the next. The blower motor used to circulate cooling air across the test samples is a constant speed motor, and accordingly, the flow rate of cooling air across the test samples is substantially constant. Consequently, the temperature of the test samples constantly changes due to corresponding changes in the ambient air temperature and changes in solar radiation intensity. It has also been discovered that changes in the temperature of the test samples can alter the rate of weathering which occurs; for example, test samples tend to weather faster in the summer than in the winter due to nominally higher test sample temperatures in the summer as a result of both higher average ambient temperatures and greater solar radiation intensity.

Accordingly, it is an object of the present invention to provide an outdoor accelerated weathering test device which is adapted to maintain the temperature of the target test samples substantially constant during daylight hours despite variations in the daytime ambient air temperature, and despite variations in solar radiation intensity.

It is another object of the present invention to provide such a test device wherein the nominal target sample temperature during daylight hours may be easily adjusted by the person conducting the test.

It is yet another object of the present invention to provide a control mechanism for accomplishing the aforementioned temperature control, which control mechanism is relatively inexpensive and easily retrofitted to existing accelerated weathering test devices.

It is a further object of the present invention to provide such an accelerated weathering test device which provides a visual indication to the person conducting the test of the temperature of the test samples mounted to the target board of the test device.

With respect to accelerated outdoor weathering test devices, it is known to provide a cover or shield which can selectively be inserted between the solar concentrator and the target board to shield the test samples from solar radiation in the event of an electrical power failure. During such an electrical power failure, the squirrel cage blower used to circulate cooling air across the test samples ceases to operate, and continued exposure to concentrated solar radiation without the benefit of such cooling could severely degrade the test samples and ruin the test. One example of such a shield is disclosed in U.S. Pat. No. 3,521,967 issued to Archer. Deployment of the shield or cover can be actuated in response to the detection of a loss of electrical power. It is also known to those in the art to provide an air flow sensor switch within the air tunnel of the test device in order to activate the deployment of the shield or cover during daylight hours whenever the flow of cooling air stops, as might result from a failure of the blower motor.

It is another object of the present invention to utilize the aforementioned control mechanism that maintains the temperature of the test samples substantially constant to also control the deployment of a shield or cover blocking further solar radiation from the test samples whenever the temperature of the test samples is significantly above the adjusted nominal test sample temperature.

These and other objects of the present invention will become more apparent to those skilled in the art as the description of the present invention proceeds.

SUMMARY OF THE INVENTION

Briefly described, and in accordance with one embodiment thereof, the present invention relates to an accelerated weathering test apparatus of the type used to concentrate solar radiation upon test samples supported by a target board, and wherein the temperature of the test samples is maintained substantially uniform during daylight hours despite variations in the daytime ambient air temperature and variations in solar radiation intensity. The test apparatus includes a solar reflector for concentrating solar radiation onto the target board for illuminating the test samples. The apparatus also includes an air circulation system for circulating cooling ambient air across the target board for cooling the test samples. The air circulation system includes a fan powered by an electrical motor for creating a flow of cooling ambient air.

In order to maintain the temperature of the test samples substantially constant during daylight hours, the apparatus of the present invention includes a temperature sensor mounted to the target board for exposure to the concentrated solar radiation and for generating an electrical signal indicative of the temperature of the test samples mounted to the target board. The present invention also includes a control mechanism electrically coupled to the temperature sensor and responsive to the electrical signal generated thereby for selectively controlling the application of electrical power to the electrical motor included within the air circulation system. In this manner, the control mechanism serves to vary the speed of the electrical motor and thereby control the flow rate of cooling ambient air circulated across the target board. When the sensed temperature of the test samples increases, the control mechanism increases the speed of the blower motor to circulate more cooling ambient air across the target board in order to lower the temperature of the test samples. Similarly, if the sensed temperature of the target samples drops below the desired nominal temperature, the control mechanism decreases the speed of the blower motor to permit the test samples to warm up.

In the preferred embodiment of the present invention, the aforementioned temperature control mechanism includes a user-operable adjustment mechanism, in the form of a control knob, for allowing a user to set a nominal or desired target sample temperature.

The preferred embodiment of the present invention also includes a bypass switch for allowing the user to operate the test device in the controlled-temperature mode as described above, or in an uncontrolled mode wherein the blower motor operates at a constant speed.

The control mechanism of the present invention also preferably includes a time delay element for temporarily allowing the application of full electrical power to the blower motor during initial start up of the test device each morning in order to more easily overcome the inertia of the blower motor when at rest.

Within the preferred embodiment of the present invention, the temperature sensor that is secured to the target board includes at least one temperature sensitive electrical component, such as a thermistor or thermocouple mounted in heat conductive relationship to a metal panel which is in turn mounted to the target board. The temperature sensitive component and the metal panel to which it is secured are then preferably coated with a black coating, such as black paint, for absorbing solar radiation reflected onto the target board.

Preferably, the test device of the present invention also includes a shield or cover movable between an inactive position which permits concentrated solar radiation to reach the target board, and a shielding position covering the target board from solar radiation. A solenoid-operated latch is used to selectively retain the shield or cover in the inactive position until its deployment is desired. The temperature controlled mechanism used to control the blower motor speed also generates an electrical output signal whenever the sensed temperature of the target board exceeds a predetermined set point temperature. The latch mechanism is responsive to the aforementioned electrical signal for allowing the shield or cover to move toward its active position in order to shield the target board from further solar radiation.

BRIEF DESCRIPTION OF THE DRAWINGS

FIG. 3 is a cross-sectional view of the test device shown in FIGS. 1 and 2 viewed through lines 3—3 as shown in FIG. 2.

FIG. 4 is a cross sectional view of the target board and air tunnel portion of the test device showing a protective cover latched in its inactive position.

FIG. 5 is a view similar to that shown in FIG. 4 wherein the protective shield has been deployed to block further solar radiation from reaching the target board.

DETAILED DESCRIPTION OF THE PREFERRED EMBODIMENT

Figure 1:
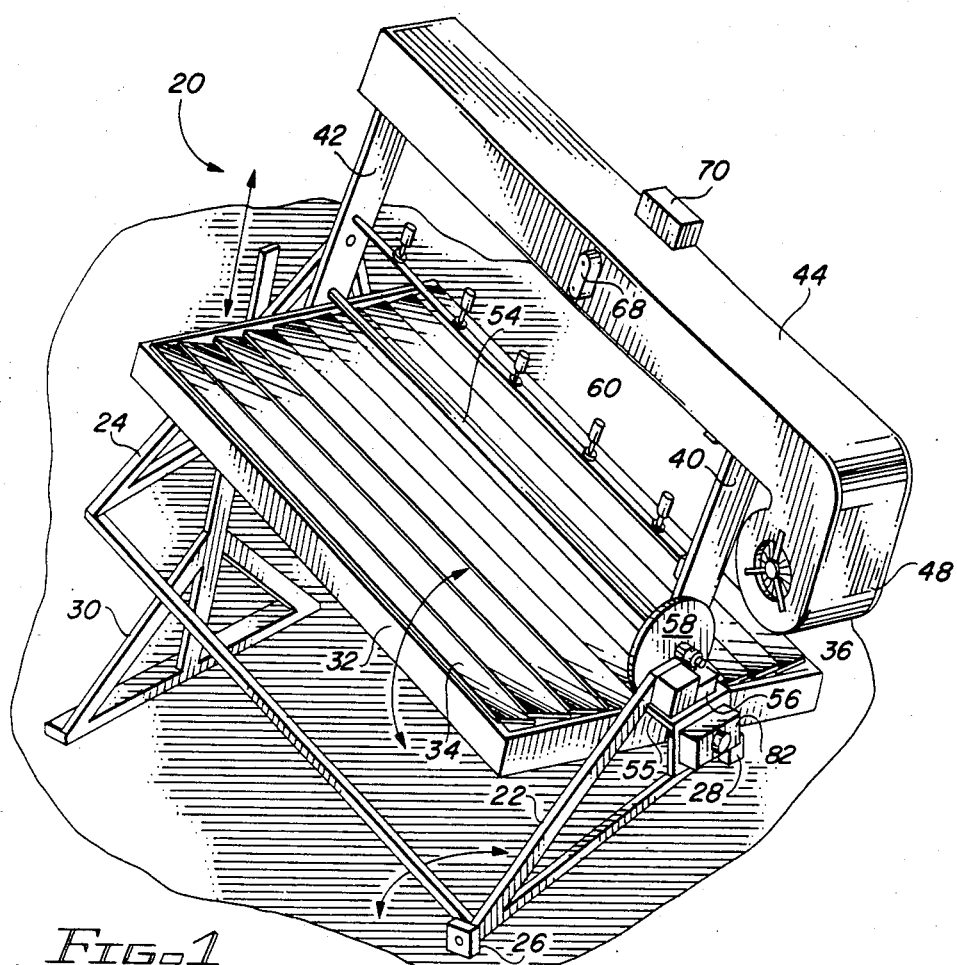
FIG. 1 is a perspective view of an accelerated weathering test device incorporating the temperature control mechanism of the present invention.

Within FIG. 1, an accelerated weathering test device is designated generally by reference numeral 20 and includes a pair of A-frame members 22 and 24 to support the operative portion of the device. The lower ends of A-frame member 22 are provided with anchors 26 and 28 for securing the test device to the ground at a desired position. An altitude adjustment mast 30 supports A-frame member 24 at a desired adjustable height to account for periodic variation in the sun's altitude at solar noon.

Rotatably supported from the upper ends of A-frame members 22 and 24 is a mirror bed frame 32 which supports a plurality of flat mirrors, including those designated by reference numerals 34 and 36. The plurality of mirrors 34, 36 are angled to reflect solar radiation directly impinging upon such mirrors to a target board 38 (see FIG. 3).

Figure 2:
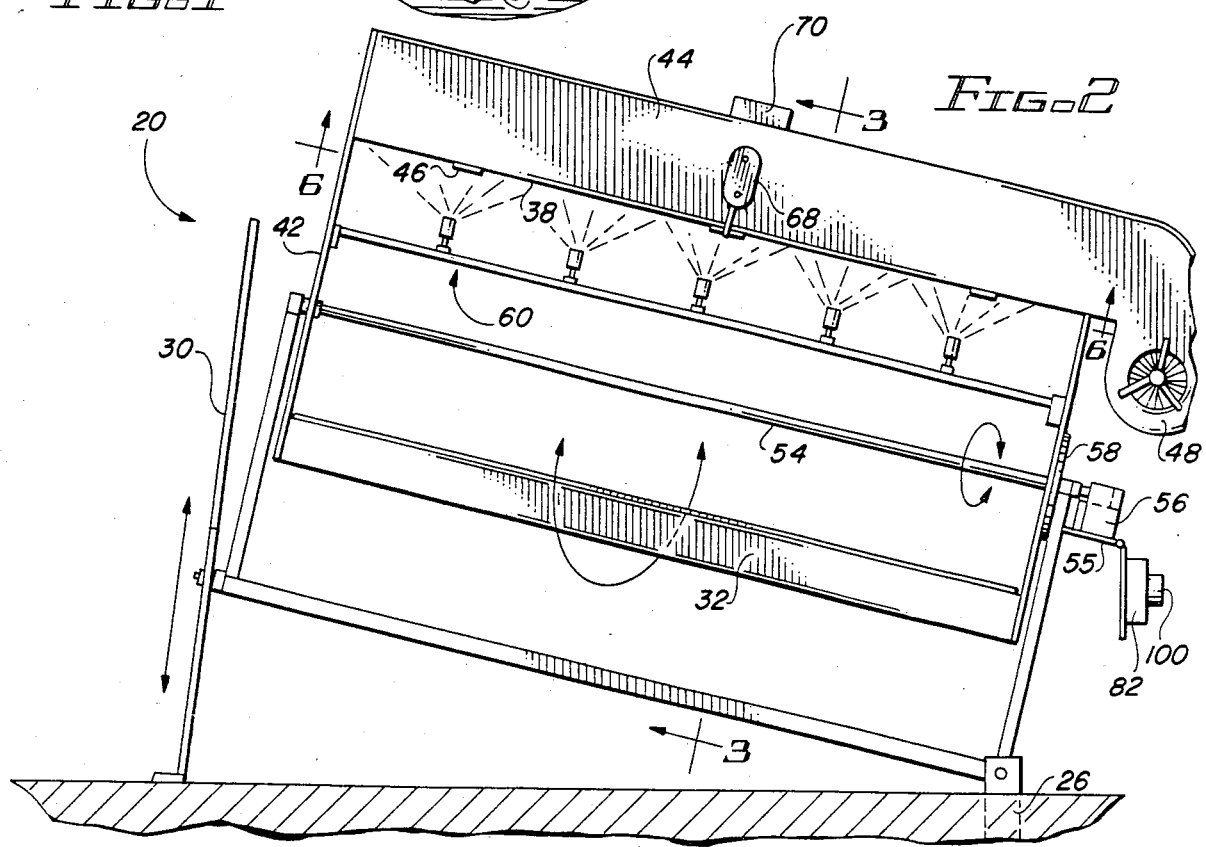
FIG. 2 is a side view of the test device shown in FIG. 1.

A pair of standards 40 and 42 extend upwardly from and perpendicular to mirror bed frame 32. An air tunnel 44 having a generally rectangular cross section is supported by the upper ends of standards 40 and 42. Referring to FIGS. 2 and 3, target board 38 is supported by the lower wall of air tunnel 44, and a plurality of test samples 46 are mounted to target board 38 for exposure to the concentrated solar radiation, represented in FIG. 3 by the upwardly extending arrows. A squirrel cage blower assembly 48 communicates with one end of air tunnel 44. Squirrel cage blower assembly 48 includes a fan driven by an electric motor to circulate cooling ambient air through air tunnel 44. As shown in FIG. 3, air tunnel 44 includes a deflector 50 which extends for the length of target board 38 and causes cooling ambient air, to be circulated across target board 38 for cooling test samples 46.

Standards 40 and 42 are rotatably supported to upper ends of A-frame members 22 and 24, the axis of rotation being indicated by reference numeral 52 in FIG. 3. A supporting shaft 54, shown best in FIG. 2, coincident with axis of rotation 52, and passing through standards 40 and 42, rotatably supports that portion of the test device which tracks daily movements of the sun. In order to properly position the Fresnel-reflecting solar concentrator comprised by mirror assembly 34, 36, and reversible electric motor and related gear drive, designated by reference number 56, are provided for periodically rotating the mirror bed and target board assembly to track movements of the sun. A clutch 58 couples standard 40 to shaft 54 to rotate the mirror assembly 34, 36 and target board assembly, while permitting manual positioning of the unit at any time to correct for any positioning errors. A solar cell tracking unit (not shown) controls the application of electrical power to reversible motor 56 in order to maintain mirror bed frame 32 perpendicular to incident rays of sunlight. The solar tracker may be of the type which includes two balanced photocells and a shadowing device mounted above such photocells for shading them. When an imbalance is detected resulting from one photocell receiving more sunlight than the other photocell, an electrical error signal is generated which is amplified and used to apply power to the drive motor 56 for rotating the unit until the photocells are again balanced, indicating that the unit is properly positioned with respect to the sun.

Also shown in FIGS. 1-3 is a water spray nozzle assembly, designated generally by reference numeral 60. As shown in FIG. 2, spray nozzle assembly 60 is used to periodically spray water at the test samples 46 to simulate dew, rain, etc.

Referring to FIGS. 3, 4 and 5, a hinged shield or cover 62 is shown coupled by a hinge 64 to the lower portion of air tunnel 44, along the edge of target board 38 lying opposite air deflector 50. A cable 66 is secured to cover 62 proximate the edge thereof opposite hinge 64; cable 66 extends across target board 38 and is wound about a spring-biased reel contained within housing 68. Tension is maintained on cable 66 by the spring-biased reel tending to close shield 62 over target board 38, as shown in FIG. 5. A solenoid operated latch 70 is normally engaged with the upper edge of shield 62 and maintains shield 62 in the inactive position shown in FIG. 4 for allowing concentrated solar radiation reflected by the plurality of mirrors 34, 36 to reach test samples 46. When electrical power is discontinued to the solenoid within latch 70, it releases shield 62, which is then closed over target board 38 due to the tension within cable 66.

Figure 6:
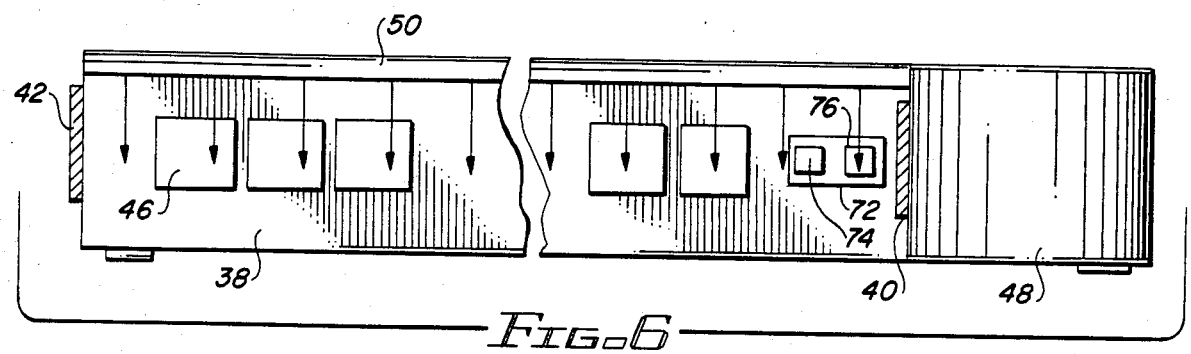
FIG. 6 is a view looking upward at the target board of the test device, as designated by lines 6—6 within FIG. 2.
Figure 7:
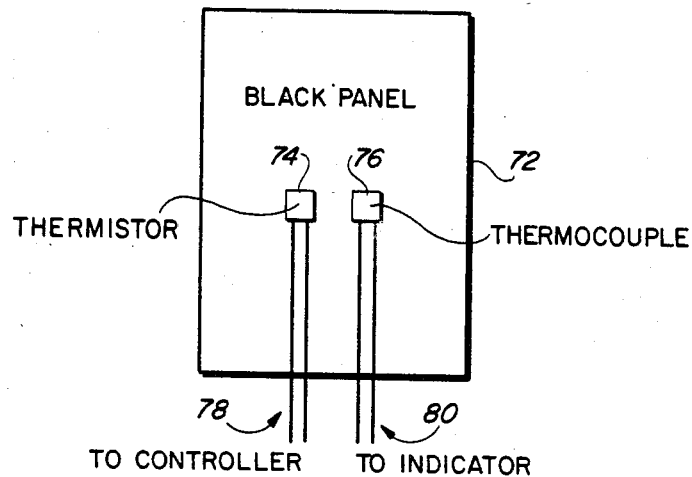
FIG. 7 is an enlarged view of the portion of the target board shown in FIG. 6 containing temperature sensitive components used to sense the temperature of the test samples mounted upon the target board.

Referring now to FIG. 6, the target board 38 is shown, including a plurality of test samples, such as 46, secured thereto. Also secured to target board 38 is a temperature sensing panel 72 having, in the preferred embodiment of the present invention, two temperature sensitive components secured in heat conducting relationship therewith, one of such components being a thermistor 74, and the second component being a thermocouple 76. Within FIG. 7 it will be noted that a pair of wires 78 lead to thermistor 74 for conducting a first electrical signal therefrom, while a second pair of wires 80 lead from thermocouple 76 for conducting a second electrical signal therefrom. Thermistor 74 and thermocouple 76 are affixed to aluminum panel 72 by an epoxy cement with high thermal conductivity. The entire assembly of panel 72, thermistor 74, and thermocouple 76 is then coated with black paint to ensure that panel 72, thermistor 74, and thermocouple 76 will absorb solar radiation impinging upon the area of target board 38 to which aluminum panel 72 is secured. An appropriate black paint which may be used for this purpose is DuPont Dulux Super Black High Temperature Enamel.

Figure 8:
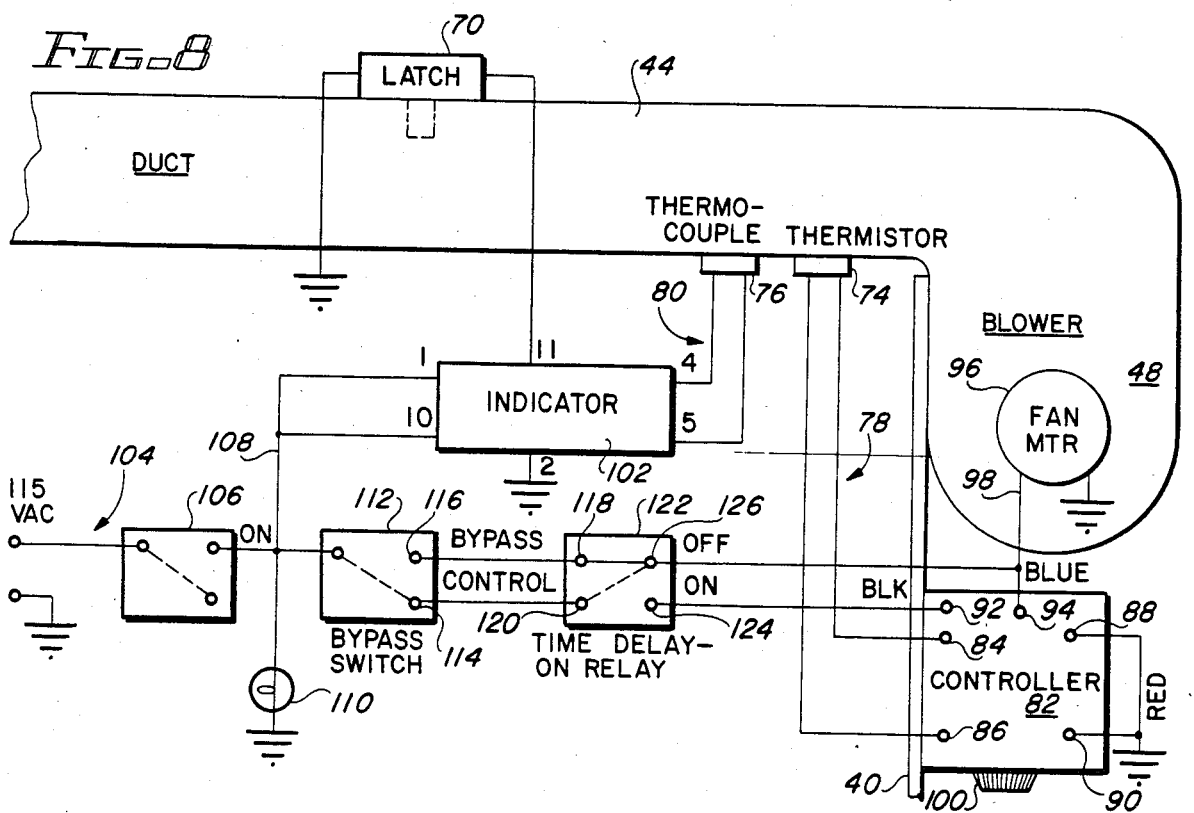
FIG. 8 is a schematic diagram illustrating the electronic control circuitry used to regulate the speed of the blower motor fan in order to achieve a substantially uniform test sample temperature.

Referring to FIG. 8, it will be recalled that the present invention includes a control circuit electrically coupled to temperature sensor panel 72 for selectively controlling the application of electrical power to the electrical motor within squirrel cage blower assembly 48. As shown in FIG. 1, controller 82 is secured to a plate 55 supporting motor/gear drive assembly 56. In the preferred embodiment of the present invention, controller 82 is a temperature modulating fan speed control of the type commercially available from Quantem Corporation of Trenton, N.J. under Model Number Series 50. The aforementioned controller 82 is a solid state, single phase, variable motor speed controller and provides control in proportion to the error sensed between an adjustable set point and the actually sensed temperature as monitored by thermistor 74. As shown in FIG. 8, controller 82 includes a pair of input terminals 84 and 86 interconnected with wire 78 leading from thermistor 74. Controller 82 also includes a pair of terminals 88 and 90 which are normally coupled to ground. Terminal 92 of controller 82 serves as the "hot" input terminal for receiving a 120 volt AC power signal. Output terminal 94 of controller 82 is coupled to one side of blower motor 96 via conductor 98. The opposite side of blower motor 96 is coupled to ground. In the preferred embodiment of the present invention, blower motor 96 is a Graingers Model Number 3M805. Thermistor 74 is preferably a TMC thermistor having a resistance of approximately 20K OHM resistance of 25° Centigrade.

Controller 82 is provided with a control knob, designated by reference numeral 100 in FIG. 8. By turning control knob 100, a user may select the set point against which the error signal generated by thermistor 74 is compared. Controller 82 serves to vary the magnitude of the output voltage supplied at output terminal 94 to blower motor 96 in accordance with the magnitude of the error described above. The temperature sensed by thermistor 74 is converted by the thermistor to a resistance which is monitored by controller 82 and compared with a reference that is determined in accordance with the position of control knob 100. Thus, the speed of blower motor 96 is increased when the temperature sensed by thermistor 74 rises above the set point temperature, while the speed of blower motor 96 is decreased when the termperature sensed by thermistor 74 falls below the set point temperature.

In the preferred embodiment of the present invention, the speed of blower motor 96 is continuously variable by controller 82. However, it is within the contemplation of the present invention to regulate the application of electrical power to blower motor 96 in a stepped fashion (high, medium, low) in order to vary the speed of blower motor 96.

Controller 82 itself lacks any means for visually indicating to the user the sensed temperature of panel 72. Accordingly, a separate indicator 102 is provided, as indicated in FIG. 8. Indicator 102 is preferably a microprocessor temperature controller of the type available from Omega Engineering, of Stamford, Conn., under Model Number CN9111. Indicator 102 includes a 3½ digit green LED readout for displaying the temperature sensed by thermocouple 76. As shown in FIG. 8, terminals 4 and 5 of indicator 102 are coupled to wires 80 for receiving the electrical signal generated by thermocouple 76. Terminal 2 of indicator 102 is grounded, while terminals 1 and 10 of indicator 102 are adapted to receive a source of 115 volts A.C.

Within FIG. 8, reference numeral 104 designates a source of 115 volts A.C. electrical power. The "hot" side of power source 104 is connected to a first side of a shut-off switch 106 which may be selectively operated by a user to switch off all electrical power to the air circulation system of the accelerated weathering test device. The opposite side of switch 106 is conducted by conductor 108 to terminals 1 and 10 of indicator 102 for supplying electrical power thereto for indicating to the user the actual temperature of the target board 38 during actual operation of the test device. The opposite side of switch 106 is also coupled to one end of indicator light 110, the opposite end of which is grounded, for providing a visual indication that electrical power is being supplied to the air circulation control system of the test device. The opposite side of switch 106 is also coupled to a first terminal or bypass switch 112 which allows the user to select either controlled operation of blower motor 96 (designated in FIG. 8 by terminal 114 labeled "CONTROL") or uncontrolled, constant speed operation of blower motor 96 (designated by terminal 116 labeled "BYPASS" in FIG. 8). Output terminals 114 and 116 of bypass switch 112 are coupled to input terminals 118 and 120 of time delay relay 122. In the preferred embodiment of the present invention, time delay relay 122 is a solid state programmable time delay relay of the type commercially available from Electric Supply, Inc. of Phoenix, Ariz., under the designation "Macromatic SS 60222 Time Ranger". A first output terminal 124 of relay 122 is coupled to input terminal 92 of controller 82 for supplying electrical power thereto. A second output terminal 126 of relay 122 is coupled to the "hot" side of blower motor 96. The purpose of time delay relay 122 is to cause 115 volts A.C. to be applied directly to blower motor 96 for a predetermined time interval to facilitate bringing blower motor 96 up to operating speed. After the predetermined time interval has passed, and assuming the controlled mode of operation has been selected by bypass switch 112, electrical power is disconnected from output terminal 126 and instead switched to output terminal 124. Accordingly, from that point forward, controller 82 regulates the voltage applied to blower motor 96.

As mentioned above, another aspect of the present invention relates to the actuation of shield 62 to cover target board 38 in the event of an overheating condition in order to protect the test samples. In this regard, indicator 102 includes an output terminal 11 which generates an output electrical signal whenever the target board temperature sensed by thermocouple 76 exceeds a predetermined set point temperature entered into indicator 102 by a keyboard (not shown) associated therewith. In the event that the actual target board temperature sensed by thermocouple 76 exceeds the preset set point limit (typically established at 5° Centrigrade above the set point entered on controller 82), then output terminal 11 of indicator 102 is switched to an open circuit, allowing latch 70 to release shield 62.

While the invention has been described with reference to a preferred embodiment thereof, the description is for illustrative purposes only and is not to be construed as limiting the scope of the invention. Various modifications and changes may be made by those skilled in the art without departing from the true spirit and scope of the invention as defined by the appended claims.

I claim:

1. An accelerated weathering test apparatus of the type used to concentrate solar radiation upon target samples, said apparatus being adapted to maintain a substantially uniform target sample temperature despite variations in the daytime ambient air temperature and variations in solar radiation intensity, said apparatus comprising in combination:
   a. a target board for supporting at least one test sample to be exposed to concentrated solar radiation;
   b. reflector means for reflecting solar radiation and concentrating the reflected solar radiation onto said target board for illuminating said at least one test sample;
   c. air circulation means for circulating ambient air over said target board for cooling said at least one test sample, said air circulation means including an electrical motor and a fan powered by said electrical motor for creating a flow of ambient air;
   d. temperature sensing means mounted to said target board for exposure to said concentrated solar radiation and generating an electrical signal responsive to the temperature thereof; and
   e. control means coupled to said temperature sensing means and responsive to said electrical signal for selectively controlling the application of electrical power to said electrical motor; in order to control the rate at which ambient air is circulated over said target board, said rate being generally increased when the temperature of said temperature sensing means rises, and said rate being generally decreased when the temperature of said temperature sensing means falls.

2. The apparatus recited by claim 1 wherein said fan is a squirrel cage blower powered by said electrical motor.

3. The apparatus recited by claim 1 wherein said air circulation means includes an air tunnel coupled to said target board, said air tunnel having an outlet extending coextensive with said target board for circulating ambient air over said target board.

4. The apparatus recited by claim 1 wherein said control means includes adjustment means for allowing a user to set a nominal target sample temperature.

5. The apparatus recited by claim 1 further including a manually operated bypass switch allowing a user to selectively bypass said control means for permitting the uncontrolled application of electrical power to said electrical motor.

6. The apparatus recited by claim 1 further including a time delay circuit for permitting the uncontrolled application of electrical power to said electrical motor for a predetermined initial time period in order to start the fan turning during initial startup of the apparatus.

7. An apparatus as recited by claim 1 including temperature indicator means for indicating to the user the actual temperature of said target board during operation of said apparatus.

8. The apparatus recited by claim 1, including:
 a. shield means moveable between an inactive position which permits concentrated solar radiation to reach said at least one test sample, and a shielding position covering said target board from said concentrated solar radiation;
 b. latch means for selectively retaining said shield means in said inactive position;
 c. said control means including output control means for generating an electrical signal when said target board temperature exceeds a predetermined set point temperature; and
 d. said latch means being responsive to the electrical signal provided by said output control means for permitting said shielding means to move toward its covering position in order to shield said target board from said concentrated solar radiation.

9. The apparatus recited in claim 1 wherein said temperature sensing means comprises at least one temperature sensor secured in heat conductive relationship to a panel mounted to said target board.

10. The apparatus recited by claim 9 wherein said temperature sensing means further includes a black coating overlying said temperature sensor and said panel for absorbing solar radiation impinging thereon.

* * * * *